United States Patent
Sakai et al.

(10) Patent No.: US 7,419,578 B2
(45) Date of Patent: Sep. 2, 2008

(54) CAPILLARY ELECTROPHORESIS APPARATUS

(75) Inventors: Tomoyuki Sakai, Kokubunji (JP); Takashi Anazawa, Kodaira (JP)

(73) Assignee: Hitachi High-Technologies Corporation, Tokyo (JP)

( * ) Notice: Subject to any disclaimer, the term of this patent is extended or adjusted under 35 U.S.C. 154(b) by 737 days.

(21) Appl. No.: 10/819,182

(22) Filed: Apr. 7, 2004

(65) Prior Publication Data

US 2004/0200723 A1 Oct. 14, 2004

(30) Foreign Application Priority Data

Apr. 11, 2003 (JP) .............................. 2003-107193

(51) Int. Cl.
*G01N 27/453* (2006.01)
(52) U.S. Cl. ..................... 204/605; 204/455; 204/603
(58) Field of Classification Search ................. 204/603, 204/452, 601, 604, 451, 453; 356/344
See application file for complete search history.

(56) References Cited

U.S. PATENT DOCUMENTS

| | | | | |
|---|---|---|---|---|
| 5,567,294 | A * | 10/1996 | Dovichi et al. | 204/603 |
| 5,570,447 | A | 10/1996 | Liu | 385/125 |
| 5,730,850 | A | 3/1998 | Kambara | |
| 6,383,356 | B1 * | 5/2002 | Hayashizaki et al. | 204/605 |
| 6,635,164 | B1 * | 10/2003 | Anazawa et al. | 204/603 |
| 6,660,148 | B2 * | 12/2003 | Shoji et al. | 204/455 |
| 6,661,510 | B1 | 12/2003 | Hanning et al. | 356/318 |

(Continued)

FOREIGN PATENT DOCUMENTS

| | | |
|---|---|---|
| EP | 1 128 182 | 8/2001 |
| JP | 8-261988 | 10/1996 |
| JP | 9-96623 | 4/1997 |
| JP | 9-152418 | 6/1997 |
| JP | 10-19846 | 1/1998 |
| JP | 2001-242140 | 9/2001 |

OTHER PUBLICATIONS

Curcio et al, "Multiplex high-throughput solid-phase minisequencing by capillary electrophoresis and liquid core waveguide fluorescence detection", Electrophoresis 2002, vol. 23, pp. 1467-1472.

(Continued)

*Primary Examiner*—Kaj K Olsen
(74) *Attorney, Agent, or Firm*—Antonelli, Terry, Stout & Kraus, LLP.

(57) ABSTRACT

A capillary array electrophoresis which can measure fluorescence of a number of capillaries at a time with high sensitivity and can automatically analyze a sample sequentially. An end edge as a sample dissolution edge of a number of capillaries is connected to a polymer filling block having a mechanism of filling the polymer as an isolation medium inside a capillary. Fluorescence irradiated from an edge surface of an end edge portion of the capillary is detected through a detection window in which distance between an external surface and a detection surface is smaller than focal distance of an optical lens closest to a detection flat surface.

7 Claims, 8 Drawing Sheets

U.S. PATENT DOCUMENTS

2002/0023839 A1 2/2002 Inaba
2003/0127328 A1* 7/2003 Nordman et al. ............ 204/451

OTHER PUBLICATIONS

Hanning et al "A liquid core waveguide fluorescence detector for multicapillary electrophoresis applied to DNA sequencing in a 91-capillary array", Electrophoresis, vol. 21, 2000, pp. 3290-3304.

Kambara, et al "Multiple-sheathflow capillary array DNA analyser" Nature, vol. 361, Feb. 11, 1993 pp. 565-566.

Anazawa, et al., "A Capillary Array Gel Electrophoresis System Using Multiple Laser Focusing for DNA Sequencing", Analytical Chemistry, vol. 68, No. 15, Aug. 1, 1996, pp. 2699-2704.

* cited by examiner

CAPILLARY ELECTROPHORESIS APPARATUS

CLAIM OF PRIORITY

The present application claims priority from Japanese application JP 2003-107193 filed on Apr. 11, 2003, the content of which is hereby incorporated by reference into this application.

FIELD OF THE INVENTION

The present invention relates to a technical field for an apparatus for separating and analyzing biomaterial such as DNA, RNA, or protein, and in particular to a technical field for capillary array electrophoresis apparatus using plural capillaries especially for sample separation column and using a fluorescence detection method as a sample measurement method.

BACKGROUND OF THE INVENTION

Electrophoresis is a basic method for separating and analyzing DNA, RNA, etc. Conventionally, a slab gel electrophoresis apparatus using slab gel having gel between two glasses as electrophoresis separation columns has been utilized. As large scale separation and analysis represented by Human Genome Project become important, however, high speed and high throughput properties have been needed for the electrophoresis apparatus. An apparatus for making real their properties is the capillary electrophoresis apparatus.

Figure 1:
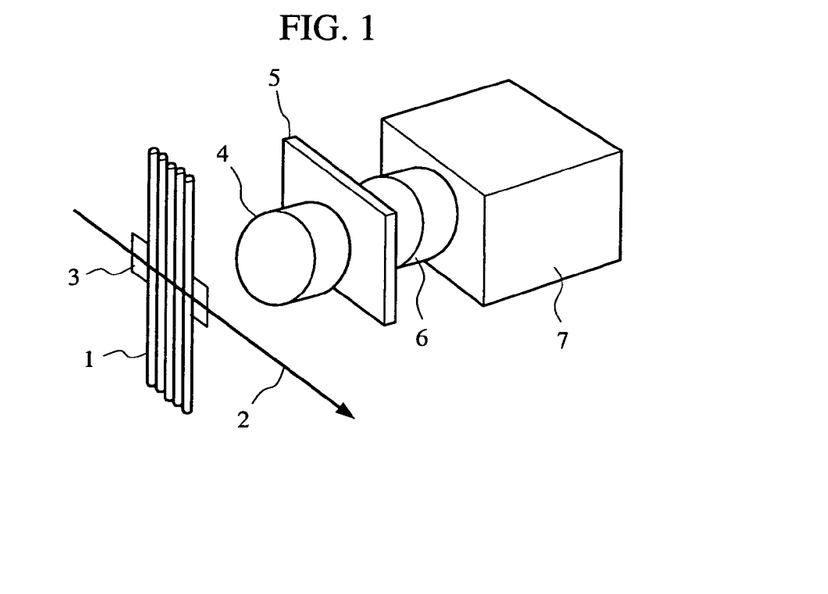
FIG. 1 illustrates an outline of a conventional capillary electrophoresis apparatus.
Figure 2:
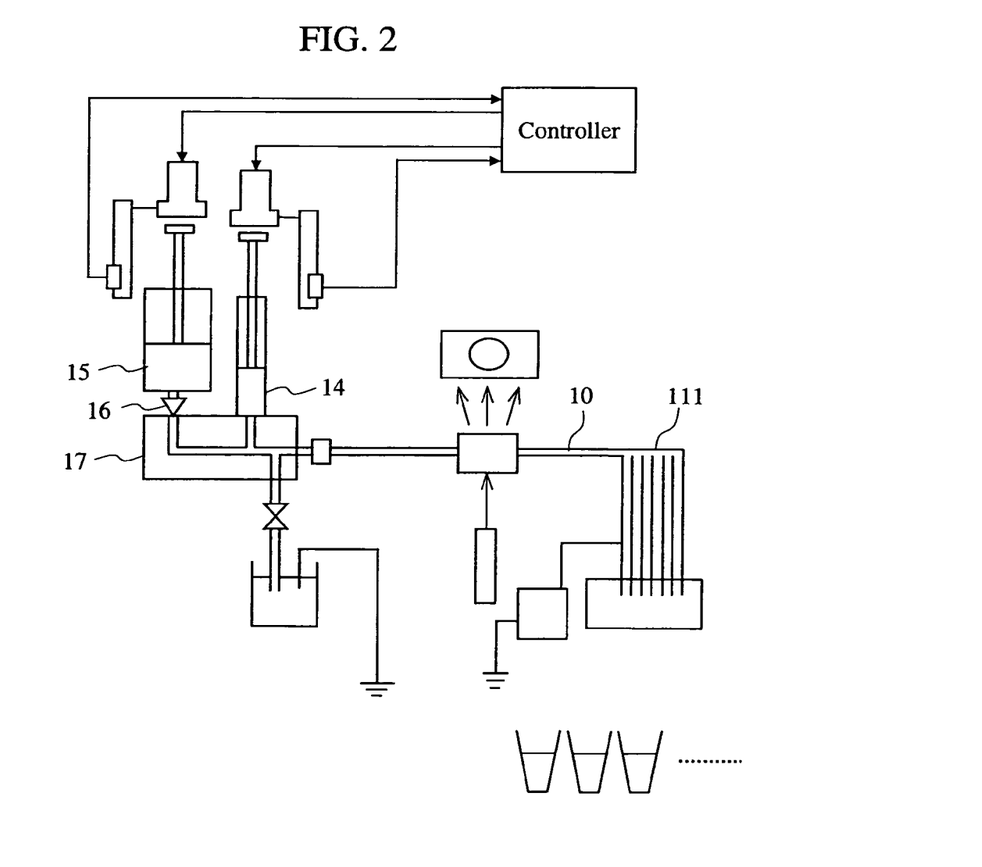
FIG. 2 is a general block diagram of a capillary electrophoresis apparatus having a conventional gel injection mechanism.

For capillary electrophoresis, the capillary array electrophoresis apparatus is described in a patent document 1, which measures on column fluorescence for detecting fluorescence from sample elements by laser irradiation toward plural capillaries simultaneously. In this device, as indicated in FIG. 1, there are provided a capillary 1, a laser beam 2, glass parallel plates 3, the first lens 4, an image splitter prism and combination filter 5, the second lens 6, a two-dimensional CCD camera 7, etc. A non-patent document 1 explains multiplex PCR (polymerase chain reaction)-mini-sequencing through capillary gel electrophoresis and liquid core waveguide fluorescence detection. A patent document 2 explains capillary electrophoresis apparatus including the capillary filled with gel beforehand and a buffer cistern provided in the lower edge portion of the capillary and detecting fluorescence from the lower edge surface of the capillary. A patent document 3 explains the electrophoresis apparatus in which lower portion of plural gel plates arranged in parallel is positioned inside a lower transparent buffering cistern and the receptor of a fluorescence detector is arranged in a facing way with the bottom face inside the buffering cistern. A patent document 4 explains that a capillary type container is used as a waveguide cell. A patent document 5 explains that a gel injection mechanism is used for injecting gel in the capillary. This gel injection mechanism includes, as indicated in FIG. 2, a block 17, an injection syringe 14 for injecting gel 10 in a capillary 11, a filling syringe 15 for filling gel 10 in an injection syringe 14, and a non-return valve 16.

[Patent document 1] JP-A No. 96623/1997
[Patent document 2] JP-A No. 19846/1998
[Patent document 3] JP-A No. 261988/1996
[Patent document 4] U.S. Pat. No. 5,570,447
[Patent document 5] Official Gazette of Japanese Patent No. 3389547

[Non-patent document 1] Johan Roeraade et al, Electrophoresis 2002 23 1467-1472
[Non-patent document 2] Anazawa, T., Takahashi, S., Kambara, H., Anal. Chem., 1996, 68, 2699-2704

SUMMARY OF THE INVENTION

Fluorescence of a number of capillaries shall be measured with high sensitivity at a time by the capillary array electrophoresis apparatus. Further, a number of samples shall be analyzed serially. However, a conventional capillary array electrophoresis apparatus cannot perform functions for such demands.

An object of the present invention is to provide, responding to the foregoing demands, a capillary array electrophoresis apparatus capable of measuring fluorescence of a lot of capillaries at a time with high sensitivity and automatically analyzing a number of samples sequentially.

In order to make real sequential automatic analysis by a capillary array electrophoresis apparatus, the polymer solution is needed to be filled in a capillary automatically. In the patent document 5, as indicated in the foregoing, a gel injection mechanism for injecting gel into the capillary is described. On the other hand, reviewing a method for measuring fluorescence with high sensitivity at a time using a number of capillaries, the method (hereinafter, referred to end detection) for detecting fluorescence from the end face of the edge portion of the capillary as described in the patent document 2 is an advantageous method because capillary extremities can be arranged in the two-dimensional way.

Figure 3:
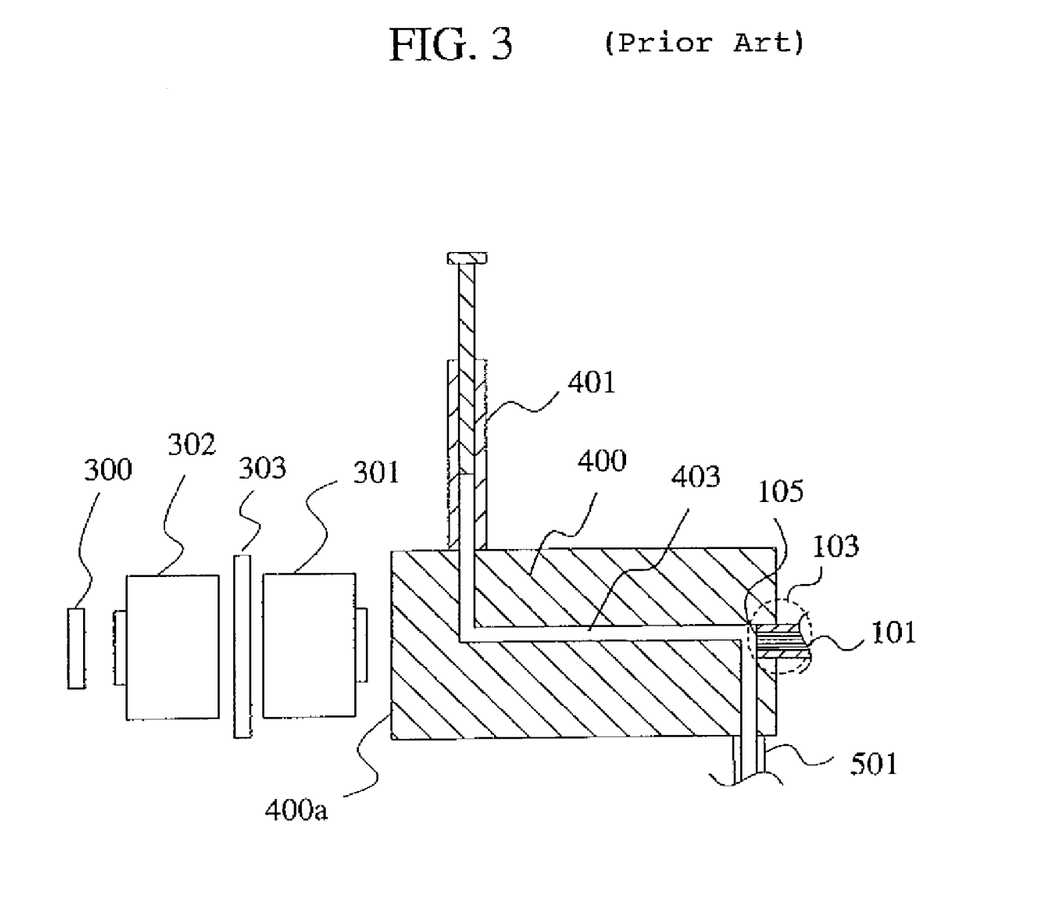
FIG. 3 is a sectional view of conventional polymer filling block.

Here, it is proposed that end detection is performed by the apparatus of the patent document 5. FIG. 3 is a sectional view of a polymer filling block 400. A polymer is filled into a number of capillaries 101 through a duct 403 by a syringe 401. In the event that end detection is performed using the polymer filling block 400, fluorescence detection shall be performed from a longitudinal direction of an end edge portion 103 of the capillary 101, namely through a left side surface 400a of the polymer filling block 400. A fluorescence detection optical system includes the first camera lens 301, the optical filter 303, the second camera lens 302, and the two-dimensional CCD camera 300. However, since material of the polymer filling block 400 is made of acryl resin, problems are caused, in which fluorescence and scattered light irradiated from acryl resin become back light and fluorescence detection sensitivity is deteriorated. Further, there is a bent opaque duct 403 between the capillary detection end face 105 and a side surface 400a inside the polymer filling block 400. Fluorescence cannot therefore be detected easily because refraction, reflection, and dispersion are caused until fluorescence irradiated from the capillary detection end face 105 reaches fluorescence detection optical system.

In general, in order to perform high sensitive fluorescence detection, although brightness of the first camera lens 301 is desirably $F \leq 1.2$, the focal distance of a marketing camera lens satisfying this condition is $f<50$ mm. Further, in order to make fluorescence irradiated from the capillary detection end face 105 to be parallel light beams by the first camera lens 301, distance L between the first camera lens 301 and the capillary detection end face 105 shall be the same as a focal distance f of the first camera lens 301. That is to say, the following numerical expression (1) shall be satisfied:

$$L = f < 50 \text{ mm} \quad (1)$$

On the other hand, distance between the capillary detection end face 105 and the side surface 400a of the polymer filling block 400 is 70 mm or more, thus the following numerical expression (2) shall be satisfied structurally:

$$L > 70 \text{ mm} \quad (2)$$

Since the foregoing expressions (1) and (2) are incompatible obviously, capillary extremity detection cannot be performed with high sensitivity using the polymer filling block 400.

In this way, the sequential automatic analysis of the patent document 5 and the capillary end detection of the patent document 2 are incompatible.

It is reported that a buffering cistern is provided in the lower part of the end face of the edge portion of the capillary or a gel plate and fluorescence is detected via the preceding buffering cistern, as described in the foregoing. In such a case, however, the capillary or the gel plate is filled with gel in advance, thus a means for injecting gel, i.e. polymer, has not been needed. Further, in the case of sequential automatic analysis having a polymer injection means, since the structure of FIG. 2 is employed, the end detection has been impossible. This invention is to provide a novel means for providing compatible sequential automatic analysis with the end detection at the time of utilizing the structure having the polymer injection means. Accordingly, a high-throughput capillary array electrophoresis apparatus can be provided, which can measure a number of capillaries at a time with high sensitivity and have capable of analyzing sequentially a number of samples automatically.

The capillary array electrophoresis apparatus of the present invention is characterized in detecting fluorescence irradiated by laser beam irradiation toward the capillary through a polymer container (polymer filling block) provided in the vicinity of an edge portion of the capillary. This polymer filling block has desirably the following characteristics.

(1) A polymer filling block material between an end face of the edge portion of the capillary and a fluorescence detection optical system is made of non-fluorescent material. Especially, the preceding material is desirably made of quartz.

(2) The end face of the edge portion of all the capillaries are arranged so as to be essentially on a flat surface, the preceding flat surface and all the boundary surfaces where a refractive index change in a polymer filling block in the preceding region are essentially in parallel, and the prescribed parallel condition does not extend beyond the range of precision tolerance.

(3) The distance between the end face of the edge portion of the capillary and the out side surface of the polymer filling block of the preceding region is less than a focal distance of the lens closest to said the polymer filling block. Especially, the preceding distance is preferably 50 mm or less.

(4) Fluorescence is detected through a polymer filling block by filling a polymer or buffering solution.

A fluorescence detection optical system may be provided in the outside of a detection window, an object lens for detecting fluorescence is installed, and the distance between the end of edge portion of the capillary and the out side surface of the detection window may be smaller than the working distance of the objective lens.

The capillary may be detachable from the polymer receptor. The capillary edge portion may have a means for positioning the position of the end face of the edge portion of the capillary for the outside surface of the detection window, and this means may be a spacer provided in. the detection window. Further, the edge portion of one side of the capillary may contact with the solution having the same refractive index as the polymer filled into the capillary. Further, plural capillaries form plural sheets which are partially or completely arranged essentially on the flat surface at the irradiation position of light of the capillary, and plural sheets may be arranged essentially in parallel with the preceding flat surface. Further, a mechanism for removing Joule heat generated inside the capillary at the time of applying voltage to the capillary can be provided in the vicinity of the edge portion of one side of the capillary. Further, the irradiation positions of light of the capillaries are partially or totally arranged essentially on the flat surface, and light may be irradiated partially or totally toward plural capillaries essentially from the parallel direction with this flat surface.

Another type capillary array electrophoresis apparatus of the present invention includes a polymer receptor of introducing the polymer or buffering solution in the vertical direction to the direction of moving the preceding polymer inside the preceding capillary.

According to the foregoing apparatus, fluorescence irradiated from the end face of the end edge portion of the capillary can be detected through the polymer filling block. As a result, fluorescence of a number of capillaries can be measured at a time with high sensitivity, and further a number of samples can be automatically analyzed sequentially.

Here, the polymer receptor, or the polymer filling block is named as a matter of convenience, and its function is not limited to the function of containing the polymer or filling the polymer. Further, the sheet formed by plural capillaries indicates the condition of arranging plural capillaries.

According to the present invention, fluorescence of a number of capillaries can be measured at a time with high sensitivity and further a number of samples can automatically be analyzed sequentially.

These and other objects, features, and advantages of the present invention will become more apparent in light of the detailed description of a preferred embodiment thereof, as illustrated in the accompanying drawing.

DESCRIPTION OF THE PREFERRED EMBODIMENTS

The following part explains the embodiments with reference to drawings.

First Embodiment

Figure 4:
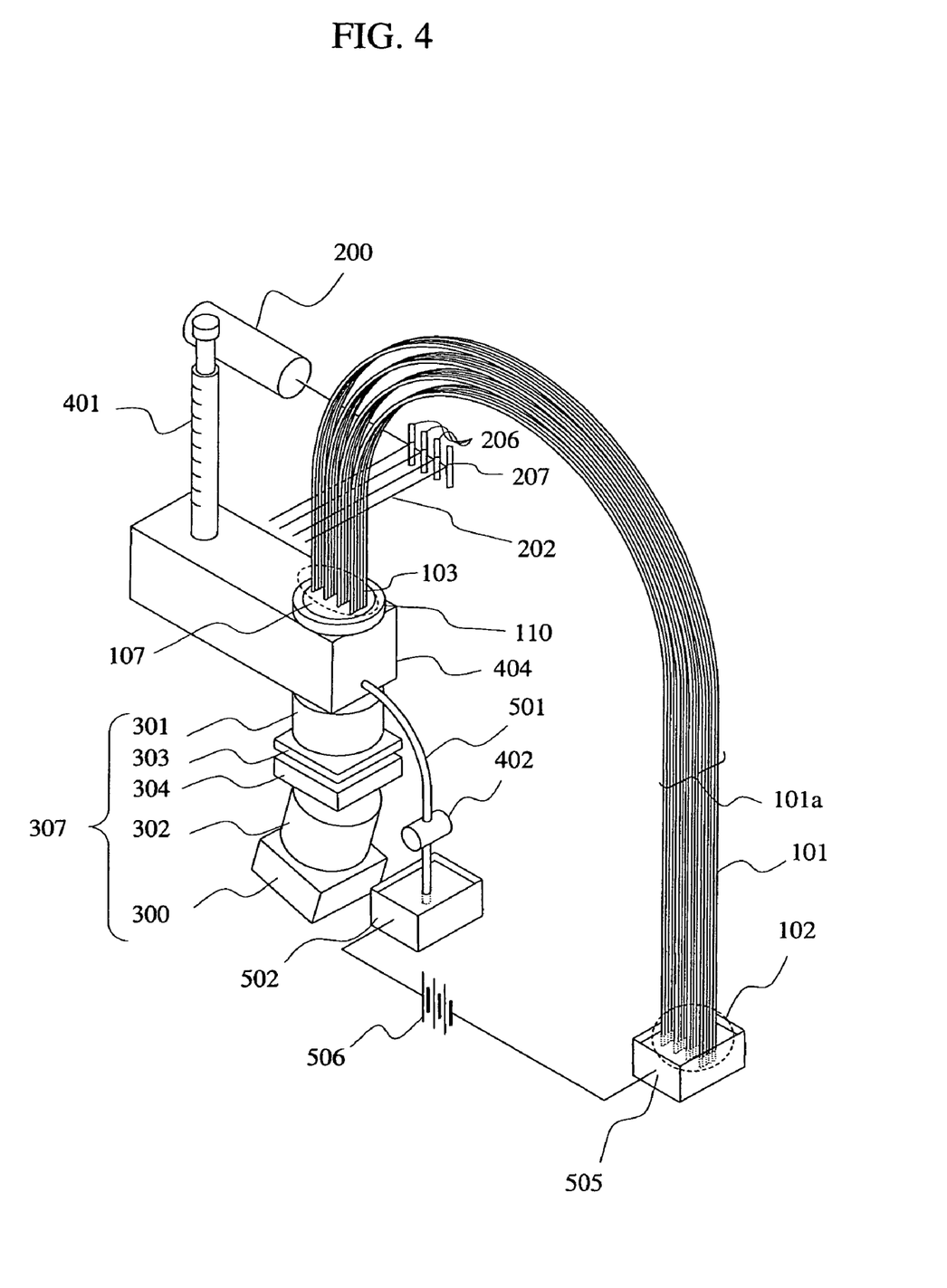
FIG. 4 exemplifies an automatic capillary array electrophoresis apparatus of the present invention.

FIG. 4 illustrates an automatic capillary array electrophoresis apparatus as an example. This example explains the way for analyzing electrophoresis of 20 capillaries at a time. 20 capillaries are bunched and form capillary arrays 101a. Each capillary 101 is made of quartz, and a polyimide coat is formed in the external surface of each capillary 101, which has a total length of 40 cm, an external diameter of 360 µm, and an internal diameter of 50 µm. Here, a capillary coated with fluorine resin can be used instead of the capillary coated with polyimide. In each capillary 101, a start edge portion 102 is a side of installing samples and an end edge portion 103 is a side of migrating and liquating out samples in the capillary by electrophoresis. A laser illumination position is a position which is 30 cm (10 cm from the end face of the end edge portion 103) from the end face of the start edge portion 102 of each capillary 101, and the polyimide coating of its capillary portion is removed. 4 sets of capillary arrays are formed by arranging the position of laser illumination by respective 5 capillaries 101. In the laser illumination position, each capillary 101 is arranged substantially in parallel with each other, and each laser illumination position of each capillary is so arranged as to become a straight line. Here, the condition in which the capillaries are arranged in parallel with each other means the degree of parallelization within the degree of precision tolerance. Further, a part of the capillaries shall be arranged in a flat face of an illumination position. This flat face shall have a flatness condition within the degree of precision tolerance. Further, the capillaries are arranged in a plural-sheets way so as to form plural sheets. Each sheet is arranged substantially in parallel with each flat face of capillary arrays. The meaning of this "parallel" is a parallel degree within the degree of precision tolerance. A laser beam 202 (wavelengths 488 nm and 515 nm, output 100 mW) irradiated from an argon ion laser source 200 is divided into 4 beams by a beam splitter 206 and a mirror 207, and then 4 sets of capillary arrays are irradiated. Each laser beam 202 is adjusted so as to be essentially parallel to each capillary array 101 and then the capillary arrays are irradiated. Here, the laser beam irradiation to each capillary essentially in parallel means that the direction of laser beam irradiation is essentially parallel to each essential flat face of respective capillary arrangements. In order to suppress the degradation of electrophoresis separability, the width of laser irradiation to the capillary arrays is desirably adjusted to the width smaller than the internal diameter (50 µm) of the capillary array 101. If the above mentioned laser irradiation is performed in a condition in which each inside of the capillary array 101 is filled with a polymer solution (Applied Biosystems, POP-4) as a separation medium, the laser beam is propagated through all the capillaries, thus all the capillaries can be irradiated effectively at a time.

Figure 5:
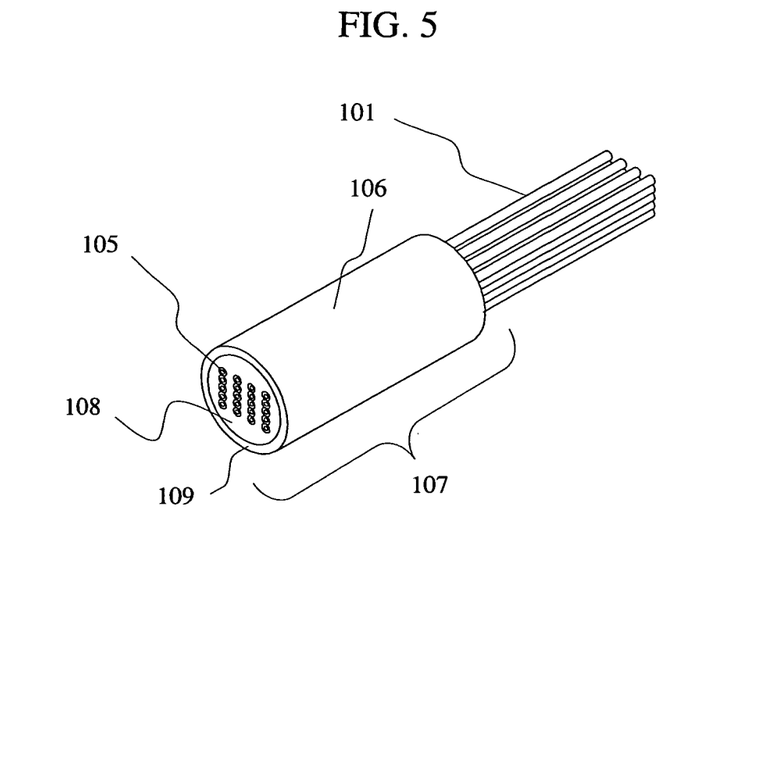
FIG. 5 is a perspective view of the vicinity of a capillary array end edge portion of the first embodiment of the present invention.

FIG. 5 is a perspective view of the vicinity of the end edge portion 103 of the capillary arrays 101a. In the end edge portion 103 of the capillary arrays 101a, 20 capillaries 101 are bundled and a capillary array head 107 is formed. The capillary array head 107 includes the end edge portions 103 of all the capillaries 101, a cylindrical fixing jig 106, and an adhesive agent 108. Here, an end face (capillary detection end face 105) of the end edge portion 103 of each capillary 101, an edge of the cylindrical fixing jig 106, and a surface of the adhesive agent 108 are arranged essentially in a flat face, thus a detection flat surface 109 is formed. Each capillary detection end face 105 is arranged in a 5×4 lattice way on the detection flat surface 109. Here, each position of the start edge portion 102 of each capillary 101 corresponds with each position of the capillary detection end face 105. Material of the cylindrical fixing jig 106 has desirably low conductivity and rigid. Further, material of the adhesive agent 108 has desirably, due to contact with the polymer solution, a water insoluble property, and has desirably high chemical stability so as not to affect separation of electrophoresis. In this embodiment, polyetheretherketone is utilized as material of the cylindrical fixing jig 106, and a silicon type adhesive agent (Cemedine Super X Black, Cemedine) is utilized as material of the adhesive agent 108.

Figure 6:
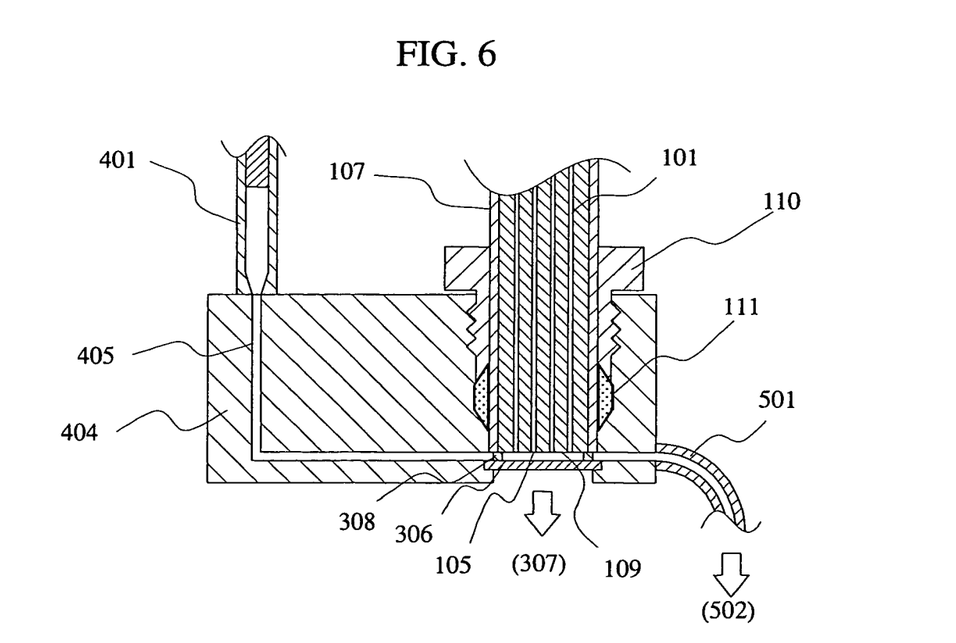
FIG. 6 is a sectional view of a polymer filling block of the first embodiment of the present invention.

As shown in FIG. 4, the capillary array head 107 is connected to a polymer filling block 404. FIG. 6 is a sectional view of the polymer filling block 404 to which the capillary array head 107 is connected. By fastening a screw 110, while a ferrule 111 is pushed toward the inside wall surface of the polymer filling block 404, the ferrule 111 fastens the capillary array head 107 at a time, thus the ferrule 111 seals a gap between the polymer filling block 404 and the capillary array head 107. This structure has pressure resistance characteristics, and this sealing can be maintained even if high pressure is applied to the inside of the polymer filling block 404. Polyetheretherketone having rigid and low conductivity is utilized as material for the ferrule 111 and the screw 110. The polymer filling block 404 is made of acrylic resin and a duct 405 is formed in its inside. The duct 405 is connected to a pressure resistance syringe 401 and a pressure resistance tube 501, and their insides are filled with the polymer solution. The tube 501 is connected to a buffering solution cistern 502 in which the buffering solution (3700 buffer, Applied Biosystems) is filled via a valve 402 as shown in FIG. 4.

A part of the duct 405 contacts with the detection flat surface 109, and the surface of the detection flat surface 109 is filled with the polymer solution. In this way, by detecting fluorescence in a condition in which the duct 405 is filled with the polymer solution, the boundary surface of refraction index changes between the duct 405 and the inside of the capillary array 101a in the capillary detection end face 105, thus reflection can be avoided while fluorescence radiated from the capillary detection end face 105 is incoming into the duct 405. Accordingly, the effect of suppressing sensitivity degradation at the time that fluorescence radiated from the capillary detection end face 105 is detected by a two-dimensional CCD camera 300. The same effect can be obtained even if the duct 405 is filled with solution, other than the polymer solution, having the same refraction index as the polymer solution. Needless to say, fluorescence can be detected even if the duct 405 is filled with the buffering solution. Further, in the portion of neighboring the detection flat surface 109 of the polymer filling block 404, the polymer or buffering solution is introduced and discharged essentially in the perpendicular direction to the direction of a polymer move in the inside of the capillary. Here, the essential perpendicular has appropriately, to put it concretely, the angular ranges from 85 degrees or so to 95 degrees or so. By arranging in this way, the polymer or buffering solution can be introduced and discharged effectively, and further the size of an apparatus can be reduced due to easiness of arranging pipes.

Fluorescence radiated from the capillary detection end face 105 can be detected by a detector 307 including the first camera lens 301 (F=1.2, f=50), an optical filter 303, a transmission grating 304, the second camera lens 302 (F=1.2, f=50), and the two-dimensional CCD camera 300 having 512×512 pixels in the lower direction of the polymer filling block 404 via a detection window 306 and the duct 405 filled with the polymer solution.

In order to reduce fluorescence and scattered light from material composing the polymer filling block 404, other than fluorescence from samples, material of the detection window 306 shall be non-fluorescence quartz glass. Optical filter for excluding back fluorescence light and exciting light may be utilized as the detection window 306. Further, the polymer filling block 404 and the detection window 306 may be integrated by making the whole polymer filling block 404 using non-fluorescence and transparent material. In this example, the distance up to the external surface of the detection window 306 from the detection flat surface 109 of the capillary array head 107 shall be 20 mm so as to be smaller than the focal distance 50 mm of the first camera lens. The detection window 306 is situated in a position between the detection flat surface 109 of the capillary array head 107, namely a region including each edge face of capillary, and the apertura of the first camera lens 301. Further, shape of cross section surface of the detection window 306, which parallel to preceding included region, may be a substantially analogous shape to preceding included region. Further, the preceding included region, the detection window 306, and the apertura of the first camera lens 301 may have different sizes in the order of the included region, the detection window 306, and the apertura of the first camera lens 301. In this case, light can be detected completely by the first camera lens 301 effectively.

Figure 7:
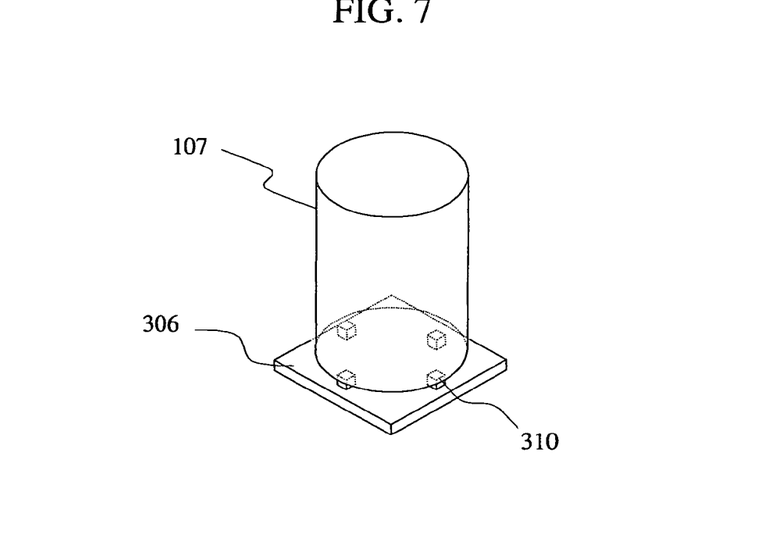
FIG. 7 is a perspective view of a detection window inside a polymer filling block of the first embodiment of the present invention.

The capillary array head 107 uses a spacer so as to enable positioning. To put it concretely, the detection flat surface 109 is pushed and contacted with 4 positioning pins 310 installed inside surface of the detection window 306 as shown in FIG. 7, thus the detection flat surface 109 can be positioned so as to be essentially parallel with the detection window 306. Accordingly, even if the capillary array is changed, the detection flat surface 109 can be connected essentially in parallel with the detection window 306 and in a preceding position repeatedly. As another way for positioning the detection flat surface 109, a step portion is formed in an outer shape in the vicinity of the detection flat surface 109 of the cylindrical fixing jig 106, and a step portion is formed in the inside wall for inserting the capillary array head 107 of the polymer filling block 404, and a step portion of the cylindrical fixing jig 106 shall be pushed and contacted with a step portion of the polymer filling block 404 so as to be fit. Accordingly, the position of the detection flat surface 109 of the capillary array head 107 to the outside surface of the preceding detection window can be positioned.

Further, according to this embodiment, the thickness of the detection window 306 is 19 mm and the length L of between the detection flat surface 109 and inside surfaces of the detection window 306 is 1 mm. If the length L is smaller than the internal diameter of the capillary 101, the duct 405 positioned between the detection flat surface 109 and the detection window 306 causes high electrical resistance, and bubbles are produced easily from the polymer solution inside the preceding duct 405 due to Joule heat at the time of applying electricity, thus electrophoresis cannot be performed. Accordingly, the preceding length L shall be larger than the internal diameter of the capillary array 101. If bubbles remain in the preceding duct 405 at the time that the capillary arrays 101a are connected with the polymer filling block 404, the valve 402 is opened and the syringe 401 is pressured, and the preceding bubbles shall be drifted toward the buffering solution cistern 502. If the preceding length L is too large, the polymer solution cannot be drifted with high speed in the preceding duct 405 at the time of pressuring the syringe 401, the preceding bubbles cannot be drifted easily, and further the quantity of the polymer solution becomes large. Therefore, the preceding length L shall be 2 mm or less. In this way, depending on the condition as an internal diameter of the capillary 101<the preceding length L<2 mm, bubbles from the polymer solution inside the preceding duct 405 at the time of applying voltage to the capillary 101 can be suppressed, and bubbles remaining in the preceding duct 405 at the time of connecting the capillary arrays 101a with the polymer filling block 404 can be drifted toward the buffering solution cistern 502 easily.

A process for analyzing samples is indicated in the following. First of all, the polymer solution inside the polymer filling block 404 is pressured by closing the valve 402 and weighing the piston of the syringe 401, and then the inside of each capillary 101 is filled with the polymer solution from the end edge portion 103 to the start edge portion 102. After the capillary 101 is filled with the constant amount of the polymer solution, the valve 402 is opened and then each start edge portion 102 of each capillary 101 is immersed in each sample solution in each well. In this condition, constant voltage is applied between the buffering solution cistern 502 and the sample solution during period of time using a high voltage power supply 506, and the sample marked by fluorescence in each well is electrically injected into each of the capillary arrays 101. After injecting samples, the buffering solution cistern 505 containing the buffering solution is moved into the position of the start edge portion 102 of the capillary 101, the start edge portion 102 is immersed in the buffering solution, voltage is applied between the buffering solution cistern 502 and the buffering solution cistern 505 using the high voltage power supply 506, and then the electrophoresis of the sample injected into each capillary 101 is performed in the direction of the end edge portion 103. At this point, attention is paid not to cause elevation difference of a solution surface between the buffering solution contained in the buffering solution cistern 505 and the buffering solution contained in the buffering solution cistern 502, so as not to move the polymer solution of the capillary 101 due to pressure difference.

Electrophoresis sample in each capillary 101 is laser-irradiated in the laser irradiation position of the capillary 101. Due to laser irradiation, fluorescence material labeled in the sample is excited, and a part of its fluorescence is reflected totally at the inside surface of the capillary 101 so as to propagate inside the capillary 101 and to emit from the capillary detection end face 105 of each capillary 101. Emitted fluorescence is passed through the detection window 306 of the polymer filling block 404, and collected and collimated by the first camera lens 301. The collimated fluorescence is passed through the optical filter 303 so as to exclude the back fluorescence and exciting light, and is passed through the transmission grating 304 so as to disperse fluorescence. And then an image of fluorescence is made on the two-dimensional CCD camera 300 by the second camera lens 302. Here, an optical prism can be used instead of the transmission grating 304 as a means for scattering wave length of fluorescence. Further, an objective lens can be used instead of the first camera lens 301. Here, in the case of using the objective lens, the same type of a high sensitive fluorescence detection system can be structured by setting the length between the detection flat surface 109 of the capillary array head 107 and the outside surface of the detection window 306 to be less than working distance of the preceding objective lens and by setting the length between the preceding objective lens and the detection flat surface 109 to be the preceding working distance. The length between the first camera lens and the capillary detection end face 105 is set to be 50 mm. An image of wavelength dispersion of the fluorescence from each capillary 101 shall be image-formed in different positions on the two-dimensional CCD camera 300. Accordingly, fluorescence from each capillary 101 can be detected separately and totally. Further, variation with time of fluorescence from each capillary 101 is measured by repeating this type of detection repeatedly. Plural kinds of samples can be analyzed by recording obtained measurement results in a computer system and by analyzing them.

Since all the preceding processes can be repeated automatically, many samples can be analyzed continuously by unmanned operation.

If stray light from the outside is entered into the detector 307 at the time of detecting fluorescence, the sensitivity of detecting fluorescence irradiated from the capillary detection end face 105 will be caused. Accordingly, regions from the laser irradiation position of the capillary 101 to the detector 307 including the polymer filling block 404 and the capillary array head 107 are desirably light-protected from the outside. In this embodiment, the whole preceding region is covered by a camera obscura. It may be covered by the camera obscura by dividing into the preceding 3 regions (laser irradiation position of the capillary 101, polymer filling block 404, and detector 317). Further, material of the polymer filling block 404 may be black acryl resin or black plastic so as to shut off stray light from the outside.

In the present embodiment, although the number of capillaries for measuring at a time is 20, the apparatus of the present invention can detect still more capillaries at a time with high sensitivity and can handle samples by unmanned operation. In order to measure fluorescence separately with high sensitivity from the plural capillary 101, the length for imaging on the two-dimensional CCD camera 300 of adjacent capillary 101 shall be the distance for 5 pixels or more, thus 102 capillaries can be arranged in the first dimensional order on the two-dimensional CCD camera 300. Further, if the number of pixels necessary for the direction of wavelength dispersion per each capillary 101 is 100 pixels, 5 or more capillary arrays 101 can be arranged in the second dimensional order on the two-dimensional CCD camera 300. In this way, for example, if capillary arrays, in which 5 capillary array sheets are changed to 96 capillary arrays and capillary arrays having 4 parallel columns of the preceding capillary array sheets are used in the present embodiment, are used, 384 capillary arrays can be measured at a time.

Second Embodiment

The object of the present embodiment is to make real easy operability of cleaning and changing the detection window by dividing the polymer filling block 404 of FIG. 4 into 2 parts of a portion having the syringe 401 and a portion having the capillary array head 107, etc.

Figure 8:
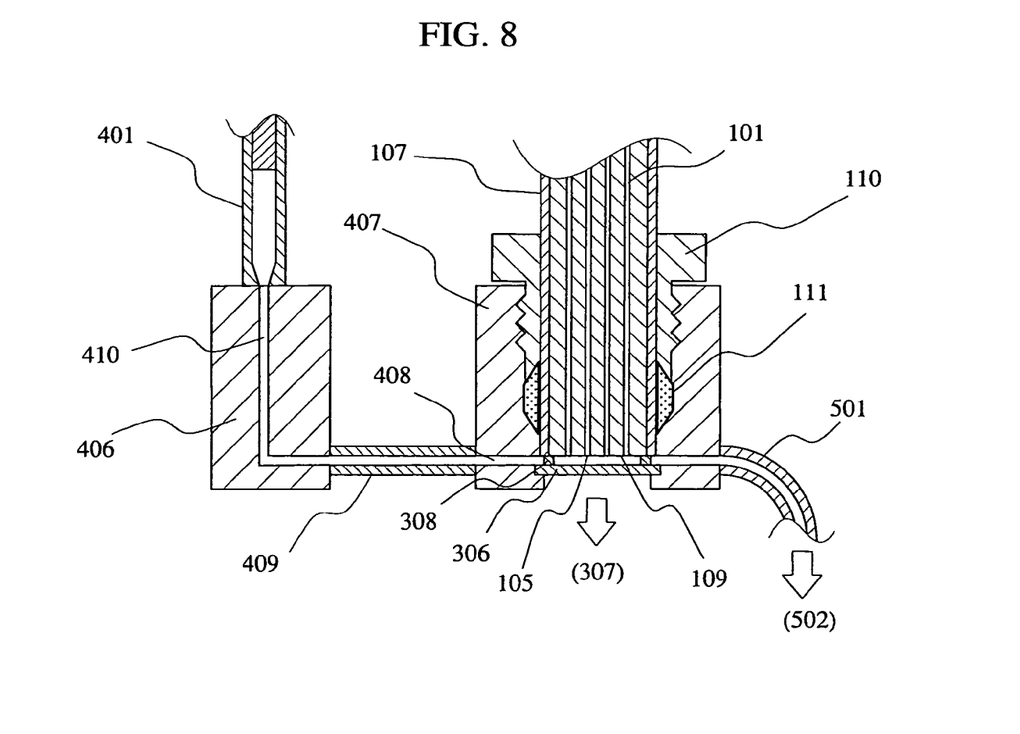
FIG. 8 is sectional view of a detection block and a polymer filling block of the second embodiment of the present invention.

In the structure of the apparatus, only the structure of the polymer filling block 404 is different from the case of the first embodiment, but the structure other than this element is the same as the case of the first embodiment. The structure of a polymer filling block 406 and a detection block 407 of installing a capillary array head 107 of the present embodiment is indicated in FIG. 8. The capillary array head 107 is connected to the detection block 407 using the screw 110 and the ferrule 111. A method of connecting the capillary array head 107 to the detection block 407 and adjustment of the position of connecting the capillary array head 107 are the same as the first embodiment. The detection block 407 is made of acryl resin, and the detection window 306 is provided in a portion located directly under the detection flat surface 109 of the capillary array head 107 as shown in FIG. 8. The detection window 306 is made of non-fluorescence quartz glass. A duct 408 formed inside the detection block 407 is filled with polymer solution. The surface of the detection flat surface 109 of the capillary array head 107 contacts with the polymer solution in the duct 408. The length between the detection flat surface 109 and outside surface of the detection window 306 shall be 20 mm, and the inside and outside surfaces of the detection flat surface 109 and the detection window 306 are set essentially in parallel with each other.

One side of the duct 408 inside the detection block 407 is connected to a duct 410 formed inside the polymer filling block 406 via a tube 409 filled with the polymer solution, and the preceding duct is connected to the syringe 401 filled with the polymer solution. Another side of the duct 408 is connected to the tube 501 filled with the polymer solution, and connected to the buffering solution cistern 502 indicated in FIG. 4 of the first embodiment. The tube 409 and the tube 501 are connected to the detection block 407 via a connector having pressure resistance, and the tubes 409 and 501 can be detached easily from the detection block 407.

According to the preceding structure, even if one of the polymer filling block 406 and the detection block 407 is contaminated, contamination can be removed by cleaning only the contaminated block. Further, although the method of covering the whole polymer filling block 404 by the camera obscura in the first embodiment is employed, the region for shielding light can be reduced in this embodiment. Further, although the size of the polymer filling block 404 is needed to be enlarged in the first embodiment so as not to cause steric hindrance of the capillary arrays 101a and the syringe 401, the preceding steric hindrance can be avoided in the present embodiment, thus the size of the polymer filling block can be lessened. Further, in the second embodiment, in the portion of neighboring the detection flat surface 109 of the capillary array of the detection block 407, the polymer or buffering solution are introduced and discharged essentially in the vertical direction to the direction of moving polymer inside the capillary. Here, "essentially in the vertical direction" means, to put it concretely, appropriately the range of angle from 85 degrees or so to 95 degrees or so. In the same way as the first embodiment, by structuring in this way, the polymer or buffering solution can be introduced and discharged effectively, and further the size of the apparatus can be lessened because tubes can be arranged easily.

Figure 9:
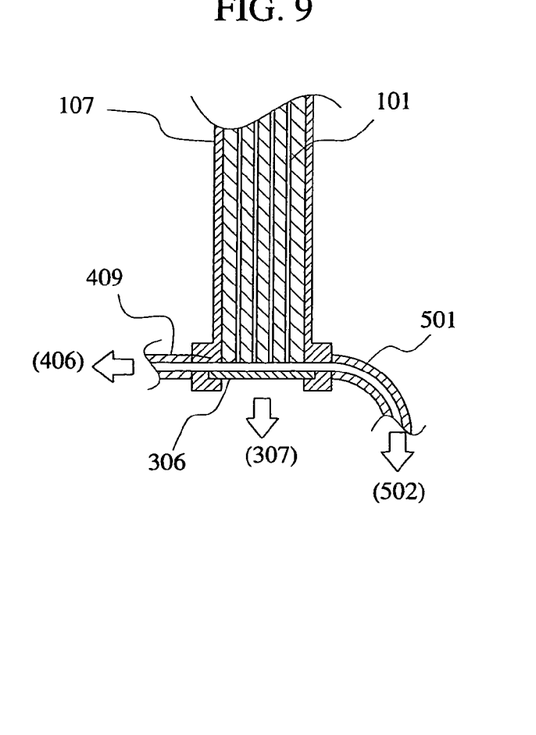
FIG. 9 is a sectional view of a capillary array head of the second embodiment of the present invention.

As the same method, as indicated in FIG. 9, there is a method of integrating the capillary array head 107 with the detection window 306 and the duct 408 between the detection flat surface 109 and the detection window 306 of FIG. 8. In the same way as FIG. 8, the tube 409 and the tube 501 are connected to the capillary array head 107 via the pressure resistance connector, and the tubes 409 and 501 can be detached easily from the capillary array head 107. In this type, the same effect as the method of FIG. 8 can be obtained.

Third Embodiment

In embodiments 1 and 2, if electrophoresis is performed by applying voltage to each capillary 101, Joule heat is generated inside the capillary 101. In the capillary array head 107 as indicated in FIG. 5, since the capillary 101 is enclosed by the adhesive agent 108, the cylindrical fixing jig 106, the polymer filling block 404 or detection block 407, effectiveness of releasing Joule heat generated inside the capillary is low. Thus, the vicinity of the capillary array head 107 becomes high temperature. As a result, the polymer solution inside the capillary 101 near the capillary array head 107 and the polymer solution of the duct formed between the detection window 306 and the detection flat surface 109 are boiled, thus bubbles may be produced. If such a condition is caused, electrophoresis performance is degraded outstandingly and further fluorescence cannot be made. Accordingly, the object of the present embodiment is to remove effectively Joule heat generated in the capillary array head 107 at the time of electrophoresis.

Figure 10:
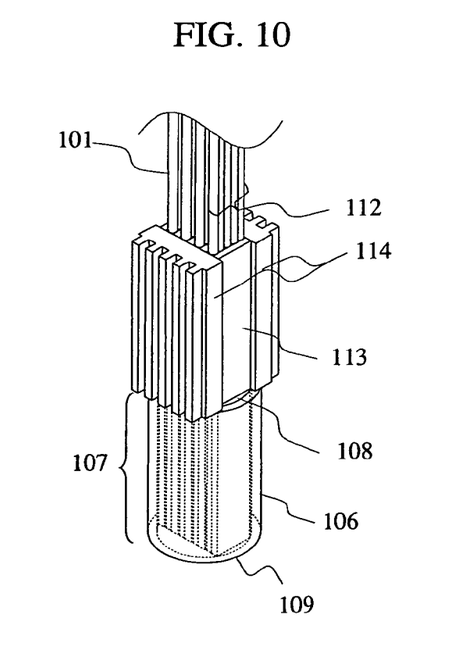
FIG. 10 is a perspective view of the vicinity of the capillary array end edge portion of the third embodiment of the present invention.

In this embodiment, the structure other than the capillary array head 107 is the same as that in the first embodiment or the second embodiment. FIG. 10 is a perspective view in the. vicinity of the capillary array head 107. The capillary array head 107 includes 4 capillary array sheets 112 formed 5 capillaries 101 as a flat surface, the cylindrical fixing jig 106, the adhesive agent 108, and 5 metal plates 113. 4 capillary array sheets 112 and the metal plate 113 are arrayed alternatively and essentially in parallel with each other. Material of the cylindrical fixing jig 106 and the adhesive agent 108 is the same as the first embodiment. The adhesive agent 108 is filled the interspace between the capillary 101 and the metal plate 113 in a fixation jig. The metal plate 113 is arranged so as not to protrude from the detection flat surface 109 in the lower side of the cylindrical fixing jig 106 and so as to protrude from the cylindrical fixing jig 106 in the upper side thereof. In this embodiment, although aluminum material is utilized for the metal plate 113, polyimide coating is performed around aluminum material so as not to cause electric current from the polymer solution contacting with the detection flat surface 109 to the metal plate 113. Ceramic material having low electric conductivity and high thermal conductivity may be used as material of the metal plate 113. All of 5 metal plates 113 are connected between 2 heat sinks 114 in the upper portion of the cylindrical fixing jig 106. Joule heat generated from the capillary 101 at the time of electrophoresis is radiated toward air from the heat sink 114 via the metal plate 113.

According to the present embodiment, Joule heat generated inside the capillary 101 at the time of electrophoresis can be removed effectively, bubbles can be suppressed from producing in the polymer solution inside the duct contacting with the detection flat surface 109, in consequence, electrophoresis and measurement of the fluorescence can be performed stably. At the time of increasing the number of capillaries for analyzing at a time and heightening voltage applied to the capillary 101, Joule thermal heat generation is increased more. Thus, the present embodiment is very effective for suppressing the preceding bubble generation especially in the preceding conditions.

In the present embodiment, although the heat sink 114 is utilized for removing Joule heat generated inside the capillary 101 at the time of electrophoresis, instead of the heat sink 114, Peltier effect material may be installed in the metal plate 113 and temperature in the vicinity of the capillary array head 107 may be controlled. Accordingly, the preceding Joule heat can be removed effectively, and further stable electrophoresis results can be obtained without being influenced by outside temperature since the temperature of the polymer solution inside each capillary 101 in the vicinity of the capillary array head 107 is stabilized.

Fourth Embodiment

In the method for laser irradiation toward the capillary 101 of the first embodiment, variation in the distance from the laser beam axis of the capillary 101 of FIG. 4 affects the effectiveness of laser irradiation toward each capillary 101.

The object of the present embodiment is to irradiate every capillary with the constant laser beam strength without causing any preceding dispersion.

The present embodiment is the same as the first embodiment or the second embodiment except an irradiation method and an irradiation position of the capillary 101 of FIG. 4. Each capillary is arranged in the vicinity of the laser irradiation position for capillary laser irradiation essentially in parallel and essentially on a flat surface. Here, "capillary essentially in parallel with each other" means a parallel degree having an accurate parallel degree within a certain precision error degree. Further, the "flat surface" means a flat surface degree having an accurate flat surface degree within a certain precision error degree. The laser beam oscillated from a laser beam source is expanded by a beam expander, converged in a line shape using a cylindrical lens, and then all the capillaries are irradiated at a time from the vertical direction to the preceding capillary array surface. Accordingly, every capillary can be irradiated with the constant laser beam strength without causing any preceding dispersion of the capillary.

Another way of laser irradiation toward the preceding capillary is described in the following. The laser beam oscillated from the laser beam source is reflected by a mirror, focused by the objective lens, and then irradiate to the laser irradiation position of the capillary. The preceding mirror and the objective lens form a driving unit and can reciprocate with high speed in the direction of arranging each capillary in the same way, thus each capillary can be irradiated by the laser beam sequentially. Further this laser irradiation method can obtain the same effects as the foregoing.

Fifth Embodiment

As a method of laser irradiation toward a plurality of capillaries of the capillary array electrophoresis apparatus at a time, there is a method (expanding method) for irradiating the capillary by expanding the laser beam irradiated from the laser beam source by a beam expander, etc. In this method, the irradiation efficiency by each capillary is about 1.7% in the case of the capillary having 150 µm in outer diameter, 50 µm in inner diameter, and 20 capillaries. On the other hand, there is a method (multi-focus method)(patent document 2), in which each capillary is arranged on a flat surface in parallel and the laser beam is irradiated from the side direction of a flat surface in which each capillary is arrayed. In this case, if the condition is the same as the preceding embodiment, irradiation efficiency by each capillary becomes 50% or so. Because the width of the preceding capillary array is 3 mm or more, the view range collecting the fluorescence of the sample in the capillary at once becomes large. Therefore, fluorescence of the sample needs to be collected using a camera lens having F value 1.4 or so. The focusing efficiency of the lens can be obtained by $1/(16 \times F^2)$, and the efficiency is 3.2% or so for F value 1.4. The efficiency of the fluorescence from the sample received by a detector such as a CCD camera can be obtained by irradiation efficiency×lens focusing efficiency. The efficiency of the fluorescence received by a detector by each capillary is 0.054% for the expanding method and 1.6% or so for the multi-focus method.

The object of the present embodiment is to heighten the efficiency of fluorescence received by the multi-focus method having high irradiation efficiency.

Figure 11:
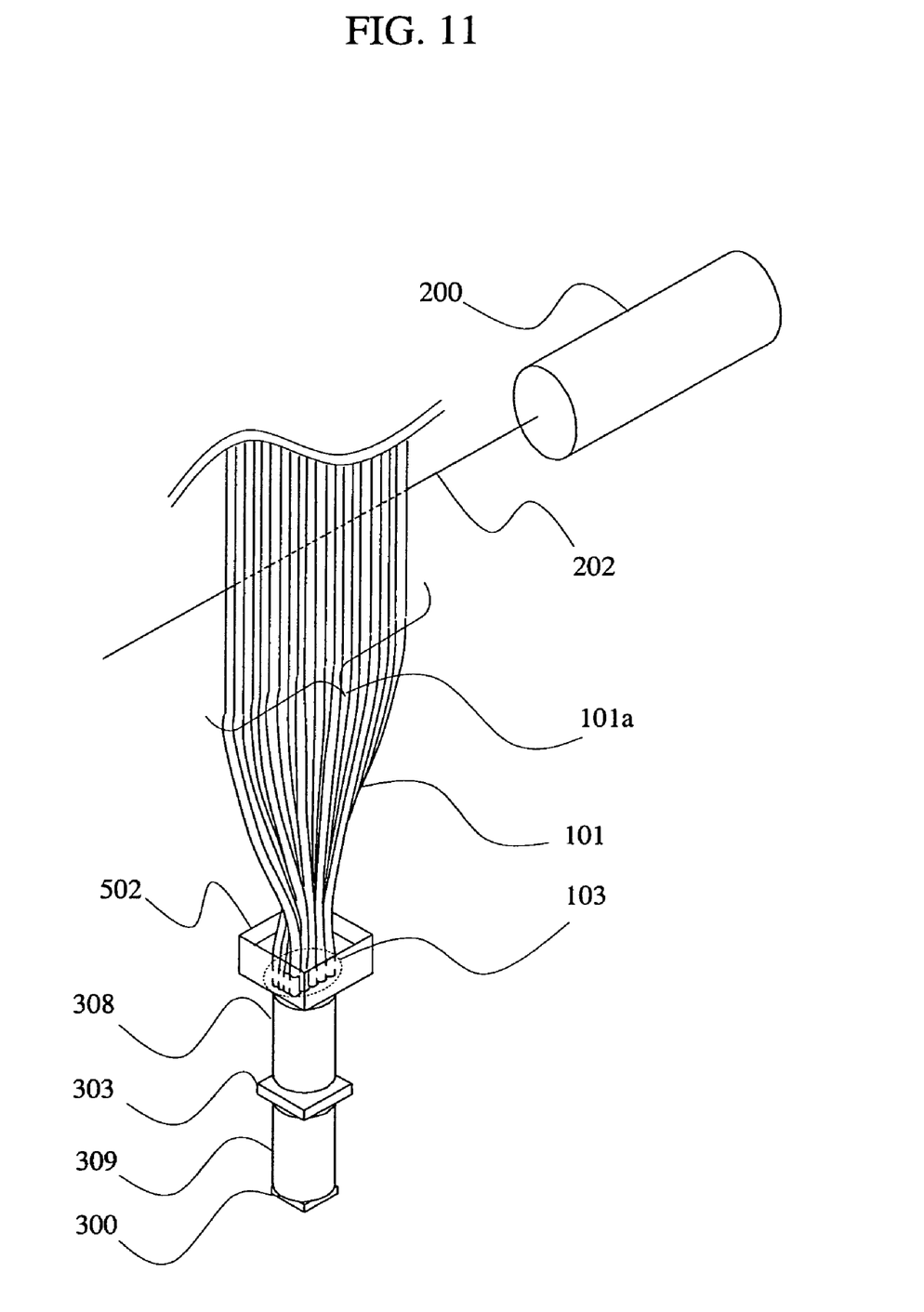
FIG. 11 is a perspective view of the vicinity of a detection region and a laser irradiation region of the fifth embodiment of the present invention.

FIG. 11 exemplifies a method for laser irradiation and detection. This embodiment is the same as the first embodiment except the used capillary, the vicinity of the capillary end edge portion, and the detector. The capillary 101 is made of quartz. The outside surface of the capillary 101 is coated with fluorine resin having a low refractive index. Each capillary 101 is 40 cm in full length, 150 μm in outer diameter, and 50 μm in inner diameter. The inside of each capillary is filled with crosslinked gel (polyacrylamid gel) as sieving matrix. A liquidity polymer solution may be used as the sieving matrix. The position locating 10 cm from the end surface of the end edge portion 103 of each capillary 101 shall be a position of laser irradiation, and the fluorine resin coating of its capillary portion is removed. The positions for laser irradiation of 20 capillaries 101 are arranged so as to form capillary arrays. Respective capillary 101 are arranged in parallel with each other, and each laser irradiation point is vertical to each capillary 101 and arranged in a straight line.

The laser beam 202 irradiated from the argon ion laser source 200 is adjusted so as to become vertical to each capillary 101 and then the capillary array is irradiated. As described in the foregoing, the irradiation efficiency of the present irradiation method by each capillary becomes 50% or so.

The end edge portion 103 is arranged in a 5×4 lattice way, the size of which is 0.75 mm×0.6 mm, thus the region for detecting fluorescence becomes very small and fluorescence focusing lens, such as the objective lens, having small F value can be used. The end edge portion 103 is immersed in the buffering solution cistern 502 filled with the buffering solution (3700 buffer, Applied Biosystems). The buffering solution cistern may be filled with the same crosslinked gel as the sieving matrix. Further, it may be filled with liquidity polymer. Fluorescence irradiated from the edge surface of the capillary end edge portion 103 is detected by the detector 307, which includes the first objective lens 308 (20 magnifications, 0.75 numerical aperture, 1 mm working distance), the optical filter 303, the second objective lens 309 (20 magnifications, 0.75 numerical aperture, 1 mm working distance), and the two-dimensional CCD camera 300 having 256×256 pixels, in the lower direction of the buffering solution cistern 502 through the buffering solution.

Bottom material of the buffering solution cistern 502 shall be quartz glass so as to reduce fluorescence and scattered light other than fluorescence from the sample. As bottom material of the buffering solution cistern 502, optical filter capable of excluding back light and excitation light may be used. In the present embodiment, the distance up to the bottom surface of the buffering solution cistern 502 from the end face of the capillary end edge portion 103 is adjusted so as to be 0.1 mm, and the plate thickness of the bottom surface of the buffering solution cistern shall be 0.5 mm so as to be 1 mm smaller than the first objective lens working distance.

The sample for electrophoresis inside each capillary 101 is laser-irradiated at the laser irradiation point. Fluorescence labeled on the sample is excited, and a part of its fluorescence is totally reflected at the inside surface of the capillary 101 and propagated inside the capillary 101 so as to be emitted from the end face of the capillary end edge portion 103. Fluorescence irradiated from the end face of the edge portion of the capillary is collected and collimated by the first objective lens 308, in the lower direction of the buffering solution cistern 502 through the buffering solution. The collimated fluorescence passes through the optical filter 303 so as to exclude back light and exciting light, and then is focused on the two-dimensional CCD camera 300 by the second objective lens 309. A transmission grating and a prism may be inserted between the optical filter 303 and the second objective lens 309, and fluorescence emitted from the capillary may be spectrometric-detected. The distance between the first objective lens 308 and the end surface of the capillary end edge portion 103 shall be 1 mm. Since the efficiency of focusing the objective lens is $1/\{16\times(1/(2\times\text{number aperture}))\}$, the lens focusing efficiency of the present embodiment becomes about 14%. Therefore, the efficiency of the fluorescence from the sample received by a detector by each capillary becomes 7%, then electrophoresis apparatus can be very sensitive according to the present embodiment.

Sixth Embodiment

A method of laser-irradiation toward the capillary in the patent document 2 for measuring fluorescence from the end terminal of the capillary is the expanding method which is described in the fifth embodiment. In the case of measuring 100 capillaries simultaneously, each of which is 150 μm in outer diameter and 50 μm in inner diameter, the efficiency of irradiation by each capillary becomes approximately 0.33% or so.

An object of the present embodiment is to increase the efficiency of irradiating a plurality of capillaries such as 100 capillaries and to measure with high sensitivity at a time.

Figure 12:
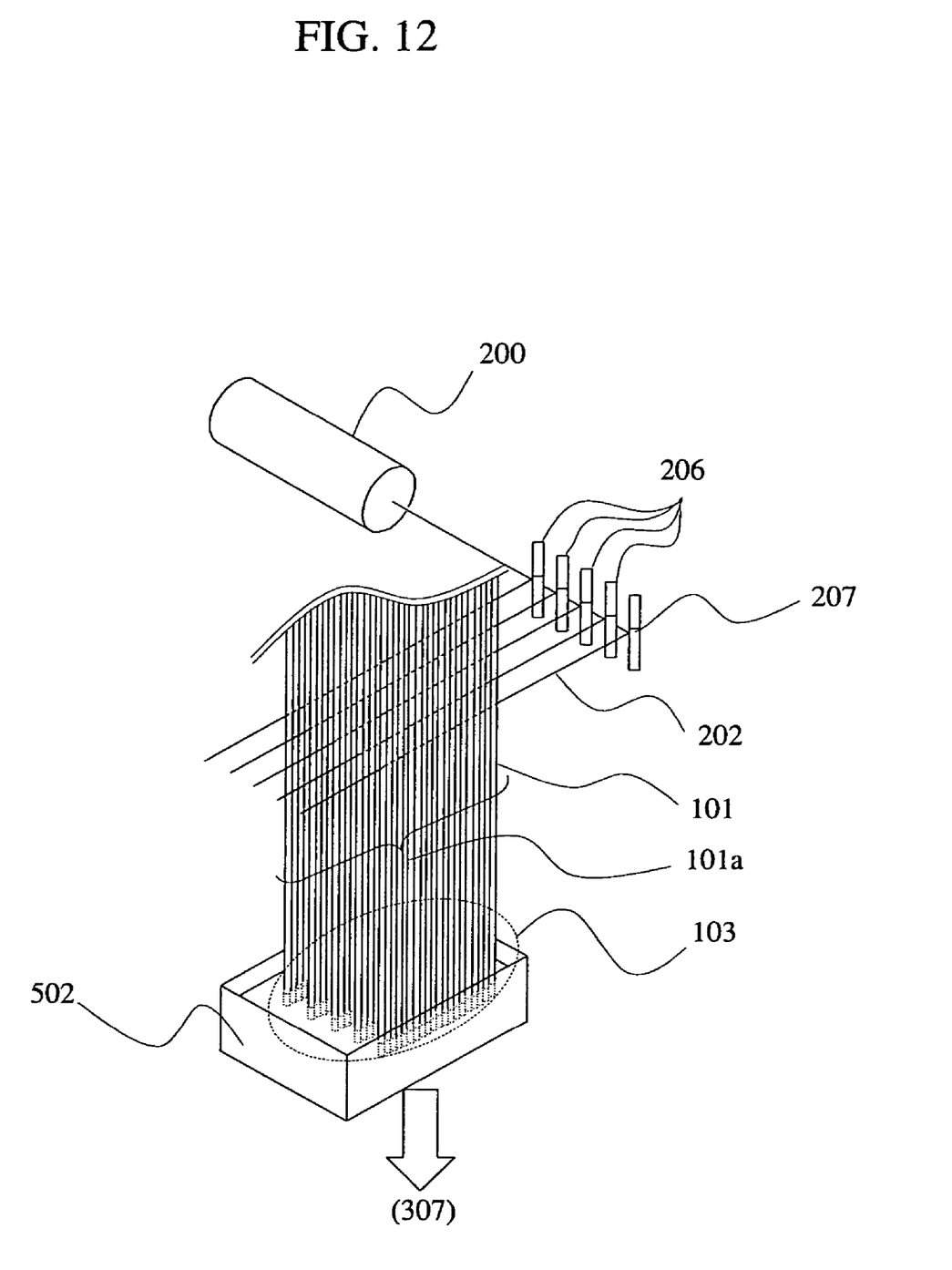
FIG. 12 is a perspective view of the vicinity of the capillary end edge portion and a laser irradiation region of the sixth embodiment of the present invention.

This embodiment is the same as the first embodiment except the used capillary and the structure in the vicinity of the capillary end edge portion. FIG. 12 is a method of laser irradiation and detection. In this embodiment, a method for electrophoresis-analyzing 100 capillaries at a time is explained. 100 capillaries are bundled so as to form the capillary arrays 101a. Each capillary 101 is made of quartz and the external surface is coated with fluorine resin having a low refractive index. Each capillary 101 is 40 cm in full length and 150 μm in outer diameter and 50 μm in internal diameter. The inside of each capillary is filled with crosslinked gel (polyacrylamid gel) as sieving matrix. The liquidity polymer solution may be used as the sieving matrix. The position locating 10 cm from the end face of the end edge portion 103 of each capillary 101 shall be a position of laser irradiation, and the capillary of its portion shall not be coated with fluorine resin. The positions for laser irradiation of respective 20 capillaries 101 are arranged so as to form 5 sets of capillary arrays. In the laser irradiation position, respective capillary 101 are arranged in parallel with each other, and each laser irradiation point is vertical to each capillary 101 and arranged in a straight line. The laser beam 202 irradiated from the argon ion laser source 200 is divided into 5 beams by a beam splitter 206 and a mirror 207 so as to irradiate 5 sets of capillary arrays from the side surface. Each laser beam 202 is adjusted so as to become vertical to each capillary 101 and then the capillary array is irradiated. The end edge portion 103 is arranged in a 20×5 lattice way, the size of which is 6 mm×6 mm. The end edge portion 103 is immersed in the buffering solution cistern 502 filled with the buffering solution (3700 buffer, Applied Biosystems). The buffering solution cistern may be filled with the same crosslinked gel as the sieving matrix. Further, it may be filled with liquidity polymer. Fluorescence irradiated from the end face the end edge portion 103 is detected by the detector 307 in the lower direction of the buffering solution cistern 502 through the buffering solution.

According to the present embodiment, the efficiency of irradiation by each capillary becomes 10% or so, and the efficiency of irradiation is 30 times higher than the expanding method. Further, a plurality of capillaries, such as 100 capillaries, can be detected by one two-dimensional detector, thus the structure of the apparatus becomes very simple.

Although the invention has been shown and described with respect to a best mode embodiment thereof, it should be understood by those skilled in the art that the foregoing and various other changes, omissions, and additions in the form and detail thereof may be made therein without departing from the spirit and scope of the invention.

What is claimed is:

1. A capillary electrophoresis apparatus, comprising:
   at least one capillary for filling a polymer;
   a polymer container being provided in a vicinity of a first end edge of said capillary;
   a polymer injector which injects said polymer into said polymer container and said capillary via said polymer container so that said polymer container and said capillary contain said polymer therein;
   a sample container being provided in a vicinity of a second end edge of said capillary;
   voltage applying means for applying voltage between said first end edge and said second end edge of said capillary;
   an irradiator for irradiating said capillary;
   fluorescence detection means for detecting fluorescence emitted from a sample via said polymer container;
   a first buffer solution cistern for holding a first buffer solution connected by a connecting portion to the polymer container; and
   a second buffer solution cistern for holding a second buffer disposed near the second end edge of the capillary;
   wherein the polymer container comprises a channel via which the polymer container, the capillary, and the connecting portion are connected, and wherein the voltage applying means applies voltage when the polymer is not substantially moved by a pressure difference between the first buffer solution and the second buffer solution.

2. The capillary electrophoresis apparatus according to claim 1, wherein plural capillaries are included.

3. The capillary electrophoresis apparatus according to claim 2, wherein said first end edge of plural capillaries are arranged substantially on a flat surface, and wherein said polymer container comprises a detection window located in between said flat surface and said fluorescence detector means.

4. The capillary electrophoresis apparatus according to claim 3, further comprising:
   an optical lens, which is provided in a vicinity of said polymer container, for detecting said fluorescence,
   wherein said detection window is positioned between a region including said first end edge of each of more than one capillary and an aperture of said optical lens and has substantially an analogous shape to said region including said first end edge.

5. The capillary electrophoresis apparatus according to claim 3, wherein said capillary and said polymer container are detachable.

6. The capillary electrophoresis apparatus according to claim 2, wherein an irradiation area comprising at least a part of a plural capillaries side surfaces arranged in an essentially planar array is irradiated, by the irradiator from a direction substantially parallel with said planar array.

7. A capillary electrophoresis apparatus, comprising:
   a capillary for filling a polymer;
   a polymer container being provided in a vicinity of a first end edge of said capillary;
   a polymer injector which injects said polymer into said polymer container and said capillary via said polymer container so that said polymer container and said capillary contain said polymer therein;
   a sample container being provided in a vicinity of a second end edge of said capillary;
   voltage applying means for applying voltage between said first end edge and said second end edge of said capillary;
   an irradiator for irradiating said capillary; and
   fluorescence detection means for detecting fluorescence emitted from a sample,
   a first buffer solution cistern for holding a first buffer solution connected by a connecting portion to the polymer container; and
   a second buffer solution cistern for holding a second buffer disposed near the second end edge of the capillary;
   wherein said polymer is introduced and discharged essentially in an orthogonal direction to a moving direction of said polymer inside said polymer container, and
   wherein the polymer container comprises a channel via which the polymer container, the capillary, and the connecting portion are connected, and wherein the voltage applying means applies voltage when the polymer is not substantially moved by a pressure difference between the first buffer solution and the second buffer solution.

* * * * *